US00PP32181P3

(12) United States Plant Patent
Lyrene

(10) Patent No.: US PP32,181 P3
(45) Date of Patent: Sep. 15, 2020

(54) BLUEBERRY PLANT NAMED 'MAGNUS'

(50) Latin Name: ***Vaccinium corymbosum* L.**
Varietal Denomination: MAGNUS

(71) Applicant: FLORIDA FOUNDATION SEED PRODUCERS, INC., Marianna, FL (US)

(72) Inventor: Paul M. Lyrene, Micanopy, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/350,811

(22) Filed: Jan. 15, 2019

(65) Prior Publication Data

US 2019/0239405 P1 Aug. 1, 2019

Related U.S. Application Data

(60) Provisional application No. 62/497,350, filed on Jan. 16, 2018.

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP10,675 | P | 11/1998 | Lyrene |
| PP12,165 | P2 | 10/2001 | Lyrene |
| PP16,404 | P3 | 4/2006 | Lyrene |
| PP26,312 | P2 | 1/2016 | Lyrene et al. |
| PP26,313 | P2 | 1/2016 | Lyrene et al. |
| PP26,523 | P3 | 3/2016 | Lyrene |
| PP26,679 | P2 | 5/2016 | Lyrene et al. |
| PP27,325 | P3 | 11/2016 | Lyrene |
| PP27,576 | P3 | 1/2017 | Lyrene |
| PP27,740 | P2 | 3/2017 | Norden et al. |
| PP27,771 | P2 | 3/2017 | Lyrene et al. |

OTHER PUBLICATIONS

U.S. Appl. No. 16/350,891, filed Jan. 29, 2019, Lyrene.
U.S. Appl. No. 16/350,892, filed Jan. 29, 2019, Lyrene et al.

*Primary Examiner* — Susan McCormick Ewoldt
(74) *Attorney, Agent, or Firm* — Dentons US LLP

(57) ABSTRACT

'MAGNUS' is a new and distinct southern highbush blueberry (*Vaccinium corymbosum* L.) variety distinguished at least by a low chilling requirement, upright growth habit, good field disease resistance, and large, firm fruit that are sweet with small, dry picking scars.

3 Drawing Sheets

Latin name of the genus and species of the plant claimed: *Vaccinium corymbosum* L.

Variety denomination: 'MAGNUS'.

BACKGROUND OF THE INVENTION

The present invention relates to a new and distinct hybrid variety of southern highbush blueberry (*Vaccinium corymbosum* L.) named 'MAGNUS'. 'MAGNUS' is a blueberry clone that can be distinguished at least by its low chilling requirement and vigorous, upright bush habit. 'MAGNUS' can also be distinguished at least by its large, firm berries that ripen from early mid-April through May when grown as a deciduous plant in north central Florida and south Georgia. 'MAGNUS' has been asexually propagated by softwood stem cuttings in Gainesville and Waldo, Fla., and the resulting plants have all been phenotypically indistinguishable from the original plant.

'MAGNUS' originated as a seedling from a cross between 'Emerald' (U.S. Plant Pat. No. 12,165) as the female (seed) parent and 'FL00-58' (unpatented) as the male (pollen) parent. This cross was made in Gainesville, Fla. in February 2001. The seedling was planted in a high-density field nursery in May 2002, and the first fruit were evaluated in April 2003. 'MAGNUS' was first asexually propagated in Gainesville, Fla. by softwood stem cuttings in 2004. After the second year of fruiting in the field, in the spring of 2004, 'MAGNUS' was propagated by softwood stem cuttings, and an experimental 15-plant test plot was established as part of a variety test at Windsor, Fla., in January 2005. At this time, the experimental code 'FL04-213' was assigned to 'MAGNUS'. Based on the growth, yield, and fruit quality of this plot, 'MAGNUS' was repropagated by softwood stem cuttings and additional experimental test plots ranging from 5 to 45 plants were established in experimental research trials. These plots have been observed during flowering and ripening each year, and no mutations or off-type plants have been observed.

'Emerald,' the female parent of 'MAGNUS', is an important variety that is planted throughout the southeastern United States. 'MAGNUS' is known to be most similar to 'Emerald'. 'MAGNUS' and 'Emerald' are distinguishable at least in their growth habit and fruit maturity date. Specifically, 'MAGNUS' displays a more upright growth habit and produces earlier fruit than 'Emerald'. Additionally, 'MAGNUS' exhibits a smaller leaf length and leaf width than 'Emerald'. 'MAGNUS' also has higher early fruit yield than its male parent, 'FL00-58'.

SUMMARY OF THE INVENTION

The following are characteristics of 'MAGNUS' when grown under normal horticultural practices in Florida.

'MAGNUS' exhibits a low chilling requirement, particularly for the flower buds; a vigorous, upright growth habit; earlier ripening; and large, firm, sweet berries with small, dry picking scars.

BRIEF DESCRIPTION OF THE DRAWINGS

This new southern highbush blueberry plant is illustrated by the accompanying photographs, which show the plant's typical form, foliage, and fruit. The colors shown are as true as can be reasonably obtained by conventional photographic procedures.

DETAILED BOTANICAL DESCRIPTION

Figure 1:
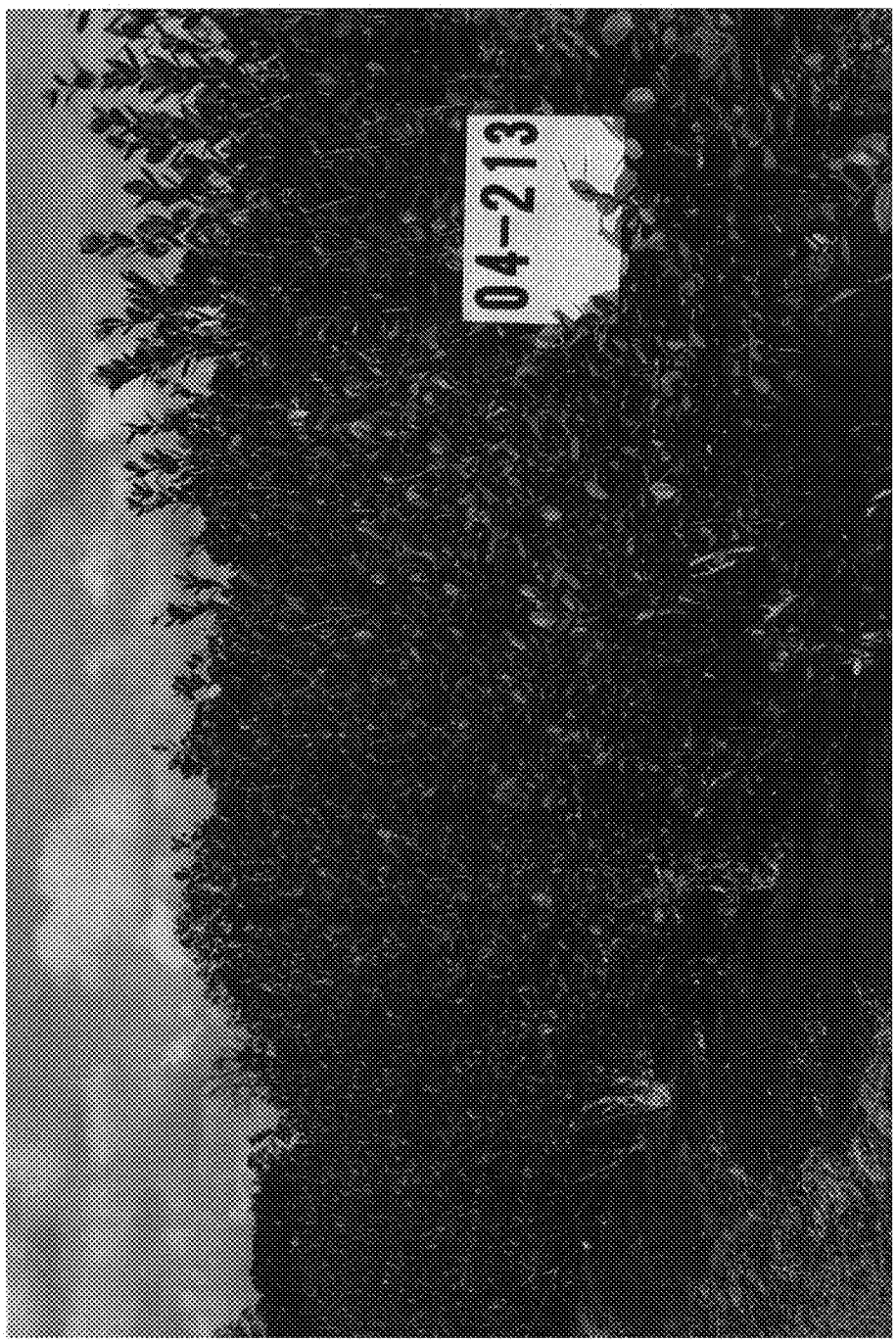
FIG. 1—Shows the plant of 'Magnus'.
Figure 2:
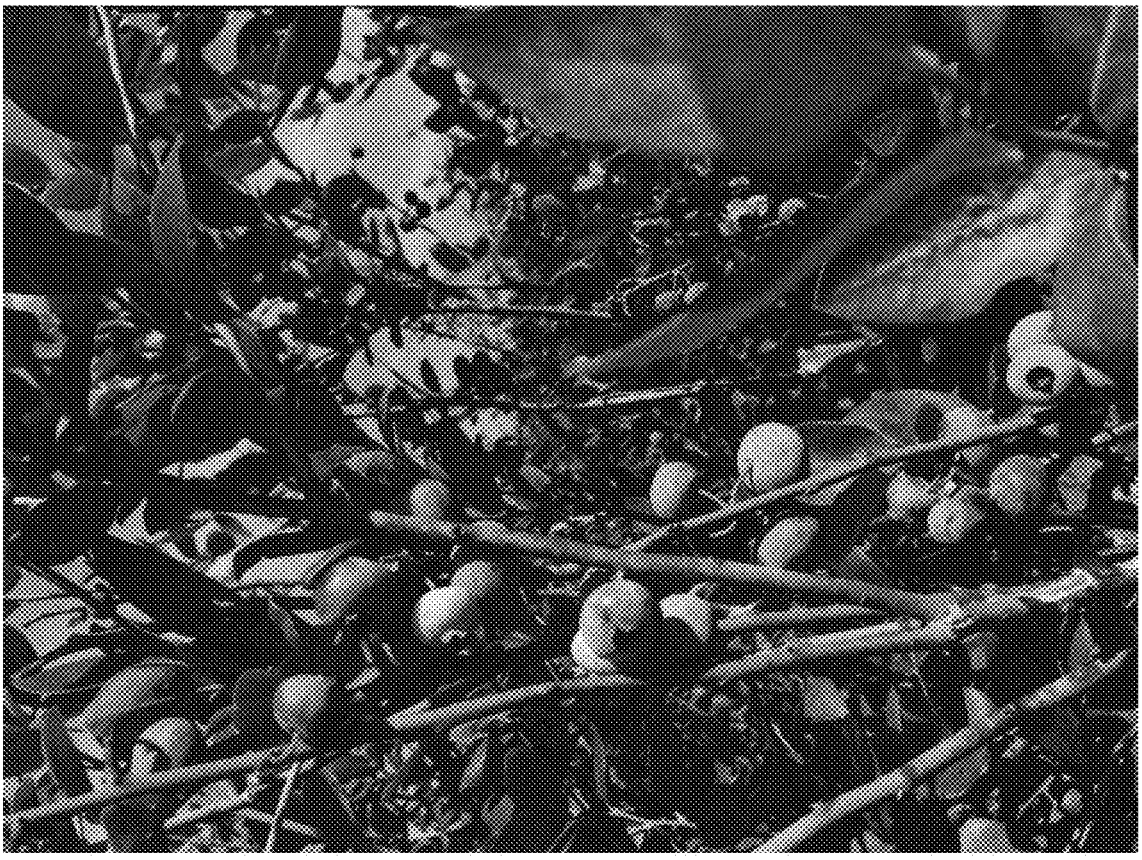
FIG. 2—Shows 'Magnus' berries during the fruit ripening season.
Figure 3:
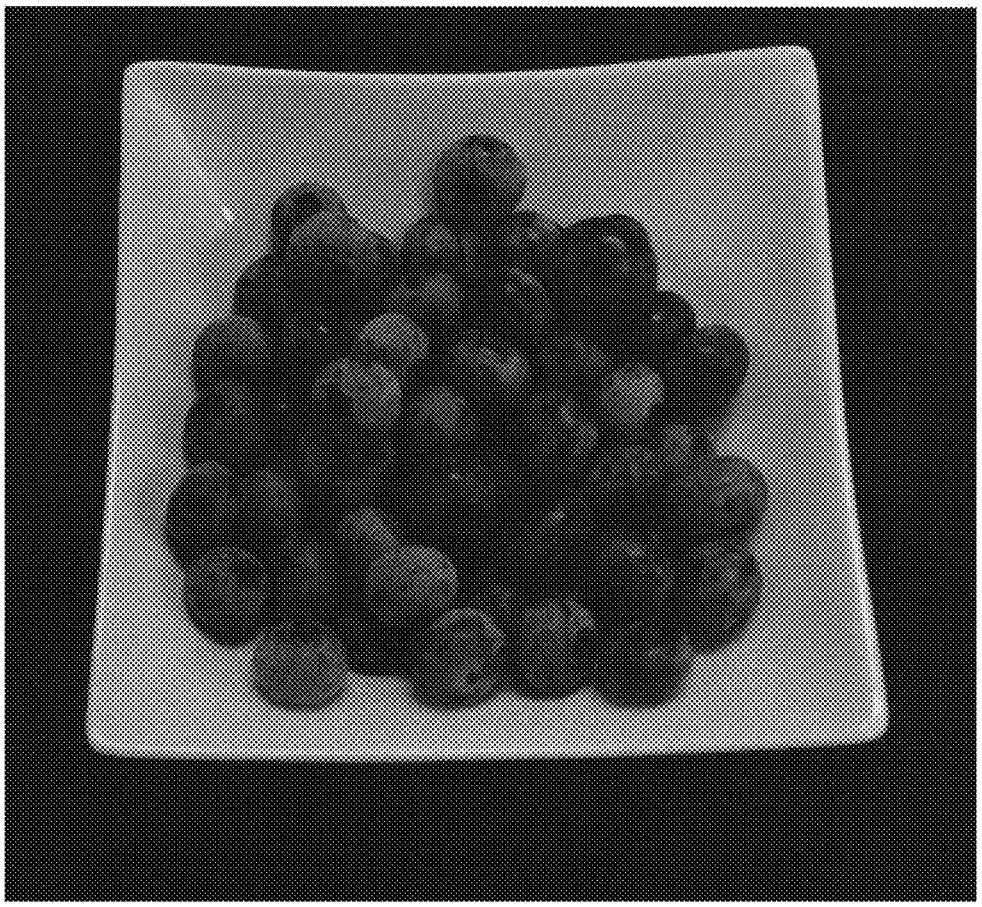
FIG. 3—Shows a close-up of harvested 'Magnus' berries.

The following detailed description sets forth distinctive characteristics of 'MAGNUS'. The data that define these characteristics were collected from asexual reproductions carried out in Florida. The plant history was taken on a plot of plants growing in an experimental trial near Windsor, Fla. The plant was 5 years of age when the data was collected. Certain characteristics may vary with plant age. 'MAGNUS' has not been observed under all possible environmental conditions, and the measurements given may vary when grown in different environments. Color descriptions are based on The Royal Horticultural Society (R.H.S.) Colour Chart by The Royal Horticultural Society, London, Fifth Edition, 2007. If any R.H.S. color designations below differ from the accompanying photographs, the R.H.S. color designations are accurate.

Classification:

*Family*.—Ericaceae.

*Botanical*.—*Vaccinium corymbosum* L.

*Common name*.—Southern Highbush Blueberry.

*Cultivar name*.—'MAGNUS'.

Plant:

*Plant vigor*.—Medium to high.

*Growth habit*.—Upright.

*Plant height*.—1.84 m on average for 5-year-old plant.

*Plant spread*.—1.49 m on average for 5-year-old plant.

*Flowers bud density along flowering twigs in January*.—High.

*Twigginess*.—Medium.

*Tendency toward evergreenness*.—Medium-Low.

*Productivity*.—3-4.5 kg per season from 5-year-old plants in Northeast Florida when hand harvested.

*Chilling requirement*.—200 hours below 7° C.

*Cold hardiness*.—Has been grown in temperate climates with extremely cold winter temperatures. Plants have survived winter freezes of −7° C. with minimal damage.

*Ease of propagation*.—Has only been propagated from softwood stem cuttings, where the rooting percentage is greater than 80% and comparable to other varieties.

Trunk and branches:

*Suckering tendency*.—Medium-Low.

*Surface texture* (*strong, 12-month-old shoots observed in October*).—Smooth.

*Surface texture* (*3-year-old and older wood*).—Moderate Rough (amount of texture and feeling of bark).

*Color of new twigs observed in the field*.—Fan 3 yellow-green group 151A.

*Color of 3-year-old, rough textured canes*.—Fan 4 greyed white group 156A.

*Internode length* (*strong, upright shoots measured in June*).—Mean of 18.7 mm.

Leaves:

*Leaf arrangement*.—Alternate, Fibonacci Spiral.

*Length*.—Mean of 5.0 cm.

*Width*.—Mean of 2.8 cm.

*Petiole length*.—Mean of 3.68 mm.

*Petiole diameter*.—Mean of 1.63 mm.

*Leaf shape*.—Elliptic, slight falcate as nearing the tip of the leaf apex.

*Leaf base shape*.—Elliptic.

*Leaf venation pattern*.—Reticulate.

*Margin*.—Entire.

*Color*.—Upper surface: Fan 3 yellow-green group 146A. Lower surface: Fan 3 yellow-green group 146B. Leaf Vein Color: Fan 3 yellow-green group 146D. Leaf petiole color: Fan 3 yellow green group 145B.

*Pubescence*.—Upper surface of leaves: No presence of hair-like structures. Lower surface of leaves: No presence of hair-like structures. Margins: Absent at all.

*Timing of vegetative bud burst* (*early, medium, late*).—Early.

*Relative time of leafing versus flowering*.—When not treated with hydrogen cyanamide in mid-winter, leafing occurs after flowering.

Flowers:

*Arrangement*.—Flowers are arranged alternately along a short, leafless, deciduous branch (90%) alternating on branches with leaves (10%).

*Fragrance*.—Slight floral fragrance.

*Shape*.—Urceolate.

*Flowering period*.—50% anthesis on Feb. 7, 2018.

*Flowers present on cluster*.—Medium.

*Flower spacing on raceme*.—Medium.

*Number of flowers per cluster*.—Mean of 5.44.

*Pedicel*.—Length at time of anthesis: Mean of 5.08 mm. Color at time of anthesis: Fan 3 yellow-green 144B with Fan 4 greyed orange group 166B on the sun exposed side.

*Peduncle*.—Length at time of anthesis: Highly variable mean of 7.37 mm. Color at time of anthesis: Fan 3 yellow-green group N144D with Fan 4 greyed-red group 181B on sun exposed side.

*Calyx*.—Surface texture: Smooth. Diameter: Mean of 6.48 mm. Color (outer surface, visible at the time of anthesis without removing the corolla tube): Fan 3 green group 138B to Fan 3 yellow-green group 145B on calyx lobes.

*Corolla*.—Diameter: mean of 7.34 mm. Length (from pedicel attachment point to corolla tip excluding the pedicel): Mean of 10.55 mm. Aperture diameter: Mean of 3.66 mm. Texture: Smooth with slight radiations. Color: Fan 4 white group 155C. Anthocyanin coloration in corolla tube: Slight.

Reproductive organs:

*Style*.—Length (top of ovary to stigma tip): Mean of 7.54 mm. Color: Fan 3 yellow-green group 144B. Location of tip of stigma relative to lip of the corolla: 1.17 mm below.

*Anthers*.—Color: Fan 4 greyed-orange group 163A. Pollen: High. Pollen germination: Typically greater 90%. Pollen Color: Fan 1 yellow group 4D. Filament length: 3.20 mm. Filament width: 1.21 mm.

*Self-fruitfulness*.—Low to medium. Planting in the field configurations that promote cross fertilization with other southern highbush varieties is recommended for all southern highbush blueberry plants grown in Florida.

Fruit:

*Mean date of* 50% *harvest in Citra, Fla*.—April 18.

*Diameter of calyx aperture on mature berry*.—Mean of 5.5 mm.

*Size and shape of calyx lobes on mature berry*.—Absent to very small, erect to incurving, with very Shallow calyx basin.

*Pedicel length on ripe berry*.—Mean of 9.2 mm.

*Detachment force for ripe berries* (*easy, medium, hard*).—Medium-hard.

*Fruit cluster density* (*sparse, medium, dense*).—Medium.

*Number of berries per cluster*.—Mean of 7.0.

*Fruiting type*.—On one-year-old and current season's shoots.

Berry:

*Cluster* (*tight, medium, loose*).—Medium.

*Weight* (*on well-pruned plants*).—Mean of 2.9 g.

*Height*.—Mean of 14.1 mm.

*Width*.—Mean of 19.5 mm.

*Shape*.—Oblate.

*Surface color of mature berries ripe on plant*.—Fan 2 violet-blue group 95C.

*Intensity of fruit bloom*.—High.

*Surface color of ripe berry after polishing*.—Fan 4 black group 203C.

*Immature berry color, with bloom*.—Fan 3 green group 142D.

*Immature berry color, without bloom*.—Fan 3 green group 143D.

*Flesh color*.—Fan 4 green and white group 157C.

*Surface wax*.—Medium to high surface wax. The surface wax on Magnus has medium to high surface wax persistence.

*Pedicel scar*.—Small and dry. Mean of 1.98 mm.

*Firmness*.—Very firm. Mean 195 g/mm.

*Flavor*.—Sweet, with some acid hints.

*Intensity of fruit sweetness*.—Medium.

*Texture*.—Good texture (firm, non-mealy flesh), and no stone cells present.

*Fruit storage quality*.—Fruit is unusually firm and can be stored without shriveling, mold or loss of firmness for 2 weeks at 4° C.

Seeds:

*Color of dried seeds*.—Fan 4 greyed orange group 177B.

*Weight of well-developed dried seeds* (25 *seeds*).—Mean of 12.8 mg.

*Length of well-developed dried seeds*.—Mean of 1.6 mm.

*Width of well-developed dried seeds*.—Mean of 0.78 mm.

Use: 'MAGNUS' produces southern highbush blueberries suitable for both the fresh and processed fruit markets.

Resistance to diseases, insects, and mites: 'MAGNUS' has grown vigorously and shows excellent bush survival in the field. It appears to be tolerant to stem blight (*Botryosphaeria* spp.) and root rot (*Phytophthora cinnamoni*), with almost no young plants dying soon after planting. 'MAGNUS' is part of the 3% of selections that survived with over 95% of plants in the plot alive after 8-years in a high disease field planting. The reaction of 'MAGNUS' to the various fungal species that cause summer leaf spots is typical of other southern highbush varieties, and fungicide applications may be needed after harvest to reduce foliar diseases and retain leaves into the fall for maximum flower bud set. Susceptibility to typical blueberry insect and mite pathogens such as spotted wing drosophila (*Drosophila suzukii*), blueberry gall midge (*Dasineura oxycoccana*), and blueberry bud mite (*Acalitus vaccini*) is similar to other southern highbush cultivars.

What is claimed is:

1. A new and distinct variety of southern highbush blueberry plant named 'MAGNUS', as illustrated and described herein.

* * * * *